(12) United States Patent
Garrec (10) Patent No.: US 11,602,419 B2
(45) Date of Patent: Mar. 14, 2023

(54) ANIMAL DENTISTRY APPARATUS AND METHODS

(71) Applicant: Mars, Incorporated, McLean, VA (US)

(72) Inventor: David Garrec, Birmingham (GB)

(73) Assignee: Mars, Incorporated, McLean, VA (US)

( * ) Notice: Subject to any disclaimer, the term of this patent is extended or adjusted under 35 U.S.C. 154(b) by 1066 days.

(21) Appl. No.: 16/144,193

(22) Filed: Sep. 27, 2018

(65) Prior Publication Data

US 2019/0090994 A1  Mar. 28, 2019

(30) Foreign Application Priority Data

Sep. 27, 2017 (GB) ..................................... 1715660

(51) Int. Cl.
*G01N 3/32* (2006.01)
*A61C 11/08* (2006.01)
(Continued)

(52) U.S. Cl.
CPC ............ *A61C 11/02* (2013.01); *A61C 11/025* (2013.01); *A61C 19/04* (2013.01); *A61D 5/00* (2013.01); *G01N 3/32* (2013.01); *A01K 15/026* (2013.01); *A61C 11/08* (2013.01); *A61C 11/088* (2013.01); *G01N 33/02* (2013.01)

(58) Field of Classification Search
CPC .......... G09B 23/28; G01N 33/02; G01N 3/32; A61C 13/097; A61C 7/36; A61C 7/00; A61C 13/08; A61C 11/08; A61C 11/088; A61C 11/02; A61C 11/025; A61C 11/001; A61C 7/08; A61C 19/04; A61F 5/566; A01K 15/026; A61D 5/00
See application file for complete search history.

(56) References Cited

U.S. PATENT DOCUMENTS 2,784,097 A  3/1957 Heyman et al.
3,032,422 A  5/1962 Alikonis
(Continued)

FOREIGN PATENT DOCUMENTS

CA   2144135 C    9/1999
CN   103558104 A  2/2014
(Continued)

OTHER PUBLICATIONS

"Meet The Chewing Robot Dog From Mars", VetX—The Vet Only Resource, Nov. 16, 2017, from https://www.vetx.com/index.php?threads/meet-the-chewing-robot-dog-from-mars.5159/, 5 pgs.
(Continued)

*Primary Examiner* — Brandi N Hopkins
(74) *Attorney, Agent, or Firm* — Morrison & Foerster LLP (57) ABSTRACT

An animal dentistry apparatus is provided and comprises a jaw assembly. The jaw assembly comprises a lower jaw and an upper jaw, and is configured such that the lower jaw and the upper jaw can move apart and together in a mastication action. The upper and lower jaw comprise at least one tooth. The apparatus further comprises a means, such as a motor, to effect the mastication action. The animal dentistry apparatus may be used to assess a chewable product, and such methods are also provided.

16 Claims, 8 Drawing Sheets

(51) Int. Cl.
  *A61D 5/00* (2006.01)
  *A61C 11/02* (2006.01)
  *A61C 19/04* (2006.01)
  *A01K 15/02* (2006.01)
  *G01N 33/02* (2006.01)

(56) References Cited

U.S. PATENT DOCUMENTS

| | | |
|---|---|---|
| 4,260,635 A | 4/1981 | Fisher |
| 4,364,925 A | 12/1982 | Fisher |
| 4,777,058 A | 10/1988 | Chandler et al. |
| 4,822,626 A | 4/1989 | Spanier et al. |
| 4,954,061 A | 9/1990 | Repholz et al. |
| D311,629 S | 10/1990 | Ragout |
| 5,182,130 A | 1/1993 | Haralampu et al. |
| 5,198,239 A | 3/1993 | Beavers |
| 5,296,209 A | 3/1994 | Simone et al. |
| 5,324,351 A | 6/1994 | Oshlack et al. |
| 5,407,661 A | 4/1995 | Simone et al. |
| 5,431,927 A | 7/1995 | Hand et al. |
| 5,449,281 A | 9/1995 | Dupart |
| 5,476,069 A | 12/1995 | Axelrod |
| 5,501,868 A | 3/1996 | Collings et al. |
| D374,753 S | 10/1996 | Tintle |
| 5,583,164 A * | 12/1996 | Jochum .......... A61K 6/887 526/323.2 |
| 5,827,565 A | 10/1998 | Axelrod |
| 5,894,029 A | 4/1999 | Brown et al. |
| 5,922,379 A | 7/1999 | Wang et al. |
| 5,935,628 A | 8/1999 | Hauser et al. |
| 6,086,940 A | 7/2000 | Axelrod |
| 6,093,427 A | 7/2000 | Axelrod |
| 6,148,771 A | 11/2000 | Costello |
| 6,200,616 B1 | 3/2001 | Axelrod |
| 6,274,182 B1 | 8/2001 | Axelrod et al. |
| D448,138 S | 9/2001 | Gokturk |
| 6,455,083 B1 | 9/2002 | Wang |
| 6,531,174 B2 | 3/2003 | Barrett et al. |
| 6,651,590 B2 | 11/2003 | Willinger et al. |
| D485,661 S | 1/2004 | Harris |
| 6,672,252 B2 | 1/2004 | Levin |
| 6,733,263 B2 | 5/2004 | Pope |
| 6,841,178 B2 | 1/2005 | Cupp et al. |
| 6,896,924 B2 | 5/2005 | Hernandez et al. |
| 6,904,870 B2 | 6/2005 | Russell-Maynard et al. |
| 7,032,541 B1 | 4/2006 | Tsengas |
| D526,641 S | 8/2006 | Haro |
| 7,087,260 B2 | 8/2006 | Axelrod |
| 7,125,574 B2 | 10/2006 | Cupp et al. |
| 7,449,204 B2 | 11/2008 | Stookey |
| 7,490,579 B2 | 2/2009 | Axelrod |
| 7,691,426 B2 | 4/2010 | Axelrod et al. |
| 7,722,911 B2 | 5/2010 | Liu et al. |
| 7,748,312 B2 | 7/2010 | Pfaller et al. |
| 7,851,001 B2 | 12/2010 | Axelrod |
| 7,879,377 B2 | 2/2011 | Dahl et al. |
| 8,137,731 B2 | 3/2012 | Pater et al. |
| 8,367,144 B2 | 2/2013 | Pater et al. |
| 8,776,729 B2 | 7/2014 | Koo et al. |
| 10,126,281 B2 | 11/2018 | Park et al. |
| 2002/0119241 A1 | 8/2002 | Speck et al. |
| 2002/0150650 A1 | 10/2002 | Cupp |
| 2002/0172752 A1 | 11/2002 | Chizmas |
| 2003/0161927 A1 | 8/2003 | Bryant et al. |
| 2003/0168020 A1 | 9/2003 | Levin et al. |
| 2003/0219516 A1 | 11/2003 | Pater et al. |
| 2004/0052906 A1 | 3/2004 | Hernandez et al. |
| 2004/0086616 A1 | 5/2004 | Nie et al. |
| 2004/0099224 A1 | 5/2004 | Russell-Maynard et al. |
| 2004/0253342 A1 | 12/2004 | Townsend et al. |
| 2006/0141009 A1 | 6/2006 | Huron et al. |
| 2006/0165854 A1 | 7/2006 | Levin et al. |
| 2006/0188611 A1 | 8/2006 | Unlu et al. |
| 2007/0172566 A1 | 7/2007 | Smith et al. |
| 2007/0224131 A1 | 9/2007 | McCollum et al. |
| 2007/0269572 A1 | 11/2007 | Turner |
| 2008/0003270 A1 | 1/2008 | Martinez |
| 2008/0063775 A1 | 3/2008 | Liu et al. |
| 2008/0064773 A1 | 3/2008 | Levin et al. |
| 2008/0124423 A1 | 5/2008 | Peterson et al. |
| 2009/0035739 A1* | 2/2009 | Alemzadeh .......... A61C 11/00 434/264 |
| 2009/0202700 A1 | 8/2009 | Bunke et al. |
| 2009/0324780 A1 | 12/2009 | Slusarczyk et al. |
| 2010/0003393 A1 | 1/2010 | Torney et al. |
| 2010/0055284 A1 | 3/2010 | Karwowski et al. |
| 2010/0266743 A1 | 10/2010 | Chen et al. |
| 2011/0076363 A1 | 3/2011 | Niehues |
| 2013/0000565 A1 | 1/2013 | Koo et al. |
| 2013/0074780 A1 | 3/2013 | Wechsler |
| 2014/0295052 A1 | 10/2014 | Elliot et al. |
| 2016/0100553 A1 | 4/2016 | Heath |
| 2016/0256247 A1* | 9/2016 | Watzke .......... A61C 11/08 |
| 2016/0327537 A1* | 11/2016 | Park .......... G01N 33/02 |
| 2018/0177156 A1 | 6/2018 | Heath et al. |

FOREIGN PATENT DOCUMENTS

| | | |
|---|---|---|
| DE | 3417196 | 11/1985 |
| DE | 20311743 | 9/2003 |
| EP | 1374700 | 1/2004 |
| GB | 1076676 A | 7/1967 |
| JP | 3-164142 | 7/1991 |
| JP | H3-164142 A | 7/1991 |
| JP | H10150925 | 11/1996 |
| JP | 2009162731 A | 7/2009 |
| JP | 2012034675 | 2/2013 |
| JP | 2014118398 A | 6/2014 |
| JP | 2015165191 A | 9/2015 |
| JP | 5919137 B2 | 4/2016 |
| KR | 20150138776 A | 12/2015 |
| WO | 01/50882 A2 | 7/2001 |
| WO | 2012156674 A1 | 11/2012 |

OTHER PUBLICATIONS

Alavi, et al., "Rheological Characteristics of Intermediate Moisture Blends of Pregelatinized and Raw Wheat Starch", J. Agric. Food Chem., vol. 50, pp. 6740-6745, Oct. 2002.

Andres, "Natural Edible Coating has Excellent Moisture and Grease Barrier Properties", Database FSTA (online), Food Processing USA, 45(13):48, Dec. 1984 (abstract 1 pg.).

Frame, "The Technology of Extrusion Cooking", Blackie Academic and Professional, 1994, Chapter 3, 46 pages.

Lawton, et al., "Viscoelasticity of Zein-Starch Doughs", Cereal Chemistry, 69(4): 351-355, Feb. 1992.

O'Donnell, et al., "Aqueous Pseudolatex of Zein for Film Coating of Solid Dosage Forms", European Journal of Pharmaceutics and Biopharmaceutics, 43(1):83-89, Jan. 1997.

Quigley, et al., "Comparative Cleaning Efficiency of Manual and Power Brushing", J. Am. Dent. Assoc., Jul. 1962, 65:26-29.

Smewing, "Texture Analysis in Action: the Volodkevich Bite Jaws", Stable Micro Systems (online), Available from: http://textureanalysisprofessionals.blogspot.co.uk/2014/10/texture-analysis-in-action-volodkevich.html, accessed Feb. 21, 2018, 3 pgs.

Turesky, et al., "Reduced Plaque Formation by the Chloromethyl Analogue of Victamine C", J. Periodontol., Jan. 1970, 41:41-43.

Warrick, et al., "A More Sensitive Method of Scoring Calculus", 11th Annual Veterinarian Dental Forum, Oct. 30-Nov. 2, 1997 Denver, USA, 5 pages.

"Food Technology Corporation: Test Cells & Fixtures", Feb. 1, 2006, pp. 1-24, XP055552439, http://www.foodtechcorp.com. Retrieved from the Internet: URL: http://pdf.directindustry.com/pdf/food-technology-corporation/test-cells-fixtures/40658-532939.html.

Anonymous, "TA.HD: When the testing gets tough, the TA.HDPlus gets going", Texture Technologies Corp. and Stable Micro Systems, Ltd. Nov. 15, 2016, XP055553121, Retrieved from the Internet:

(56) References Cited

OTHER PUBLICATIONS https://web.archive.org/web/20161115160827/http:/texturetechnologies.com/texture-analyzers/ta-hd-texture-analyzer, 7 pgs.

* cited by examiner

ANIMAL DENTISTRY APPARATUS AND METHODS

CROSS-REFERENCE TO RELATED APPLICATIONS

This application claims priority to United Kingdom Application Serial No. GB 1715660.5, filed on Sep. 27, 2017, the entirety of which is hereby incorporated by reference herein.

FIELD

The present invention relates to an animal dentistry apparatus and methods of using the same to assess a chewable product.

BACKGROUND

Chewable products can be used to promote oral hygiene of animals. The chewing, or mastication, action allows the chewable product to mechanically clean the teeth of the animal and so assist in the removal of plaque and calculus from the teeth to contribute to dental hygiene.

In developing these chewable products it is useful to understand their mechanical properties, since these can give an insight into the potential tooth cleaning performance. Existing methods of mechanical testing include impacting chewable products with cylindrical probes so as to understand the resistance that they provide to the mastication action.

When it is envisioned that a product may exhibit favorable properties, an in vivo study can provide further insight into the dental efficacy associated with the chewable product. However, such in vivo studies are time and cost intensive and rely on the availability of testing panels along with any potential ethical constraints that may exist in testing products on living beings.

The present invention aims to address the shortcomings with existing testing methods for chewable products.

BRIEF DESCRIPTION

The present invention provides an animal dentistry apparatus. The apparatus comprises a jaw assembly, the jaw assembly further comprising a lower jaw and an upper jaw. The jaw assembly is configured such that the lower jaw and the upper jaw can move apart and together in a mastication action. Either or both the upper and lower jaw may comprise at least one tooth, and the upper jaw, lower jaw and/or tooth/teeth may be ex vivo, or artificial. The tooth or teeth may be coated, in whole or partially. A means of effecting the mastication action, e.g., a hand or foot operated mechanism such as a lever, pulley or crank, or a motor such as the motor included in a Universal testing apparatus, is provided. The hand or foot operated mechanism or motor is desirably capable of imparting a normal load of up to at least 50 kg to the jaw assembly.

The animal dentistry apparatus may be used in a method for assessing a chewable product, and the same is also provided. The method comprises the steps of (i) providing a jaw assembly, wherein the jaw assembly comprises a lower jaw and an upper jaw, wherein the jaw assembly is configured such that the lower jaw and the upper jaw can move apart and together in a mastication action, and wherein the upper jaw comprises at least one tooth and a lower jaw comprises at least one tooth; (ii) placing the chewable product between the upper jaw and the lower jaw of the jaw assembly; and (iii) moving the jaws relative to each other in the mastication action in order to impact the at least one tooth of the upper jaw and the at least one tooth of the lower jaw onto the chewable product. Although the upper jaw, lower jaw and/or tooth/teeth may be ex vivo, or artificial, at least a portion of the jaw assembly is artificial and/or manufactured.

This method enables visualization and assessment of the chewable product when impacted by teeth in an upper and lower jaw, and visualization of the teeth when impacting the product. This is more akin to how the product will interact with teeth when consumed by the animal and so gives a better idea compared to previous mechanical testing approaches of how the chewable product will affect oral hygiene. It also allows a more accurate assessment of the forces that are required to chew the product. Further, this approach allows products to be pre-screened prior to in vivo tests and so avoids incurring unnecessary time and cost of conducting in vivo testing on unsuitable products.

BRIEF DESCRIPTION OF THE DRAWINGS

The invention will be described further in relation to the following figures.

DETAILED DESCRIPTION

As used herein a "chewable product" is any product that is intended to interact with animal teeth. It may be food product that is intended to be consumed, or it may be a product that is intended to be chewed but not consumed (such as an inedible chew). The term chewable product as used in relation to animal consumption encompasses edible chews, kibbles or other dry food products, or wet food products. In general, any food product that can be chewed (i.e. non liquid) can be utilized with the present invention.

In relation to animal products, the calorific and nutritional contribution to the animal's diet is a differentiating feature between a 'chew' and a 'food'. Specifically, a conventional animal 'food' is nutritionally complete and provides the full range of the animal's daily nutrition requirements. It is also intended to be the major source of the animal's calorific intake.

A 'chew' is further distinguished from a 'food' with regard to its size. The largest pieces in a food product are smaller than the size of a chew. For instance, WO-01/50882-A discloses a food product which is reported as having a large size compared to other dried pet food, and discloses several examples. The largest of these examples is a triangular kibble having the following dimensions: thickness 16 mm, base 28 mm and sides 32 mm. This is in contrast to an animal chew, which has a largest dimension which is significantly larger. As used herein, a chew is an individual piece having a largest dimension of at least about 50 mm, preferably at least about 60 mm, and preferably at least about 70 mm.

A chew is further distinguished with regard to the time taken to consume a piece of chew compared to a piece of food. Normally the consumption time for a piece of chew is much longer than a piece of food. A piece of food may generally be consumed in less than 30 seconds by an average sized dog, whereas a chew would take at least 30 seconds, may be at least 45 seconds, may be at least 90 seconds for an average-sized dog to consume, and a chew considered herein would typically take at least 200 seconds, more typically at least 300 seconds for an average-sized dog to consume.

As noted above, the jaw assembly comprises a lower jaw and an upper jaw. At last a portion of the jaw assembly is manufactured or artificial. That is, an ex-vivo jaw bone from an animal may be used, as may one or more real teeth isolated from an animal. All that is required is that some portion of the jaw assembly is manufactured or artificial. The term "lower" and "upper" are used herein to denote the different jaw members and convey, in a non-limiting way, the preferred orientation during use. However, the jaw assembly could be used with the lower jaw positioned above the upper jaw.

The lower jaw and the upper jaw are arranged as the jaw assembly in such a manner that the lower jaw and the upper jaw can move apart and together in a mastication action. In other words, the upper jaw and the lower jaw can be moved relative to each other in a manner corresponding to a chewing action. In this way, the jaw assembly can move in such a way to resemble the movement of the jaw of an animal that is intended to chew the chewable product. This allows consideration of how a pair of moveable jaws will interact with a chewable product.

The lower jaw and the upper jaw of the jaw assembly are connected, directly or indirectly, together in such a way to allow the mastication action.

The upper jaw comprises at least one tooth. The tooth is a protrusion from the jaw that can interact with a chewable product. In this way, the general interaction of a tooth with a chewable product can be investigated using the jaw assembly. The tooth preferably corresponds to a tooth of the animal of interest. In other words, the tooth's geometry is substantially the same as the geometry of a tooth of the animal. For example, the tooth may be a replica of a specific tooth of interest from the animal. Alternatively, the tooth could be an actual tooth isolated from a specimen of the animal. In this way, the jaw assembly can provide an insight into the interaction of an animal's teeth (via actual teeth or replica teeth) with the chewable product.

The lower jaw comprises at least one tooth. The at least one tooth in the lower jaw may, independently of any features of the tooth in the upper jaw, have the features cited in relation to the tooth of the upper jaw given herein. The presence of a tooth in the upper jaw and a tooth in the lower jaw allows insight into how the mastication action of the jaw causes these teeth to interact with the chewable product and so provide insight into the chewable product's contribution to the oral hygiene of the animal.

The jaw assembly may be formed from a material or materials selected from a wide range of candidate materials known to the skilled person. In particular, the jaw assembly may be formed from a metallic material. Such a metallic material can exhibit good mechanical properties enabling repeated use of the same jaw assembly. Specific potential metallic materials include steel and titanium. Alternatively, the jaw assembly can be manufactured from a plastic material. Specific potential plastic materials include polycarbonate and latex.

The jaw assembly may be formed from several different materials. In particular, the teeth can be formed from a different material relative to the rest of the jaw assembly. The teeth may be formed from a material that has mechanical properties that correspond to the mechanical properties of the teeth of the animal of interest. In this way, the effect of a chewable product on the mechanical integrity of a tooth can be investigated. For example, it could be investigated whether a particular chewable product resulted in fracture of teeth. Therefore, the teeth may be made from an artificial material that replicates the properties of real teeth, such as hydroxyapatite. Alternatively, and as noted above, real ex vivo teeth, and/or ex vivo jaw bones may be used. All teeth present may be formed of the same material. Alternatively, the teeth may be made of different materials depending on the particular investigative needs.

A tooth may be removable from the rest of the jaw assembly. In this way, the tooth can be replaced as required, or a host of different teeth can be tested individually in the same jaw assembly by switching them as required. A removable tooth may be secured by an interference fit within the rest of the jaw assembly. All teeth present may be removable. Alternatively, only some of the teeth may be removable depending on particular investigative needs.

The jaw assembly can be manufactured in various manners. For example, when a material that melts on heating is used for the jaw assembly, it can be cast. Alternatively, metallic or plastic materials can be manufactured using selective laser sintering (3D sintering). 3D sintering/printing can be especially useful where complex shapes are required, such as a replica of an animal's teeth. Further, the jaw assembly can be handcrafted.

As noted above, the method of the present invention comprises the step of placing the chewable product between the upper jaw and the lower jaw of the jaw assembly when the jaw is in an open position and then moving the jaws relative to each other in the mastication action in order to impact the at least one tooth of the upper jaw and the at least one tooth of the lower jaw onto the chewable product. In this manner, the chewing action of the animal is replicated and so the method can provide an insight into how the chewable product interacts with the teeth of the animal.

As described herein, the method can be used for assessing a chewable product that is chewed by an animal. The reference to animal is not particularly limiting. However, the present invention is particularly preferred to be directed to assessing a chewable product for a non-human animal. The present invention is particularly directed in relation to non-human animals, since they are not typically compliant and so it can be difficult to fully assess how a chewable food product interacts with the teeth of such an animal in vivo. Animals of particular interest for the present invention are canines or felines.

The placing of the chewable product between the upper jaw and the lower jaw is preferably done to ensure that the chewable product is positioned so as to interact with at least one of the teeth that are present.

The movement of the jaws relative to each other can be effected manually. In other words, the lower jaw and the upper jaw can be moved relative to each other by hand or foot action. This allows direct control of the mastication action. However, for greater control, it may be preferred to have a means for effecting the mastication action as described herein. This should also allow for the application of a greater force.

When moving the jaws relative to each other in the mastication action it is ensured that the at least one tooth of the lower jaw and the at least one tooth of the upper jaw impact the chewable product. In this way, the interaction of the teeth with the chewable product can be assessed. The impaction of the teeth with the chewable product can be ensured by the correct placing of the chewable product initially or can be ensured by moving the chewable product while the jaws are moving. In particular, the chewable product can be moved when the jaws are open during the mastication action to be placed in a new position ready for the closed portion of the mastication action. (The mastication action in this way can be considered as a sequential series of the jaw moving to an open position followed by the jaw moving to a closed position followed by the jaw moving to an open position etc.).

When referring to "open position" and "closed position", these terms refer to relatively open and relatively closed. The actual closed position can be varied to replicate a tooth separation as seen in the animal of particular interest when its jaws are closed, i.e. the closed position may still maintain a gap between the at least one tooth in the upper jaw and the at least one tooth in the lower jaw. The open position then has a greater gap between these teeth relative to the closed position.

The jaw assembly can be configured to move from an open position to a closed position until a threshold load is reached. This replicates the real life chewing situation, where an animal has a certain bite force and will accordingly bite further into a relatively soft product compared to a relatively hard product. For example, the threshold load may be 50 kg of normal load, or 100 kg of normal load, or 250 kg of normal load, or 500 kg of normal load, or 600 kg or normal load or 750 kg of normal load. The jaw assembly can be configured to move from an open position to a closed position until a threshold load is reached or a certain separation between the teeth is reached, whichever occurs first.

The placing of the chewable product and any further holding or moving of the chewable product during the testing procedure can be carried out by hand. For example, a chew can be held from one end by the operator of the jaw assembly and then held in position within the jaw so that the other end is impacted by the teeth of the jaws.

The jaw assembly may further comprise a holding means by which the chewable product is held in position. This can take form of a clamp that is attached to a stand and can be positioned relative to the upper and lower jaw so as to hold the chewable product in the desired position. The holding means may further be able to move. Therefore, the holding means is able to move the chewable product relative to the upper and lower jaws and so thus change the areas of the upper and lower jaws that are interacting with the chewable product. It is particularly preferred that the moving of the holding means is automated and carried out according to a set program with the movement being effected by motors. This automation allows for replication of the interaction between the chewable product and the upper and lower jaws across different experiments and so improves the consistency and comparability of the results.

The method of the present invention may further comprise the step, prior to step (ii), of providing a coating on the at least one tooth in the upper jaw and/or the at least one tooth in the lower jaw.

The presence of a coating can enable the external properties of the tooth to be tailored to assist with assessing the chewable product.

The coating on the tooth can fully cover the tooth. Alternatively, the coating on the tooth may only partially cover the tooth. This partial covering can be in the area of interest.

It is particularly preferred that the coating is a coating that mimics the behavior of plaque or calculus on the teeth. In other words, it is a coating that can be affected by the mechanical interaction of the tooth with the chewable product. Accordingly, the coating can be removed by the application of mechanical action. In particular, the coating may be able to be removed by the application of a normal force of less than 4 newtons moved across the surface of the tooth. This force is consistent with the force generated by a tooth brush when removing plaque, and in the range of the force required to remove calculus from companion animals. The use of a coating that mimics the behavior of plaque or calculus allows insight into how the chewable product would affect plaque on the teeth of the animal of interest.

The coating may be present on particular teeth of interest or on all teeth that are present in the jaws. The presence of the coating on all teeth in the jaws allows assessment of the chewable product in relation to all teeth that are present in the jaws.

As noted above, the coating is provided prior to the step of placing the chewable product in-between the upper jaw and the lower jaw of the jaw assembly, thus ensuring that the coating is in place before impacting the teeth on the chewable product.

A coating that has been found to mimic plaque is acrylic paint. In particular, a slow drying acrylic paint, such as OPEN acrylic paint, commercially available from GOLDEN Artist Colors, Inc., 188 Bell Road, New Berlin, N.Y. 13411-9527, can be particularly suitable. The properties of the acrylic paint can be adjusted by varying the amount of time that the coating is provided on the teeth prior to interaction with the chewable product, or by blending paints with different drying times. The amount of time that is elapsed will affect the amount of drying that the coating has undergone and thus its mechanical properties and, in particular, the ease with which it can be removed.

The method of the present invention preferably comprises the further step of, after step (iii), assessing the coating that was provided prior to step (ii). This assessment of the coating allows conclusions to be drawn about how the chewable product mechanically interacts with the teeth of the upper and lower jaws.

The assessment of the coating may involve comparing the coverage of the coating after step (iii) with the coverage of the coating before step (iii). This allows a quantitative and/or qualitative assessment of the effect of the chewable product on the teeth. The coverage of the coating that is assessed may be the total coverage of the coating before relative to the total coverage of the coating after. Alternatively, the comparison may be based of the coverage of the coating in a particular location of the teeth. For example, the comparison of coverage may be along a particular line of interest.

A particularly preferred comparison of the coverage is along a line near the base of the tooth, i.e. where the tooth is joined to the rest of the jaw assembly. The line may be at an equivalent position to the gum line of the animal of interest. In this way, the effect of the chewable product on the removal of plaque along the animal's gum line can be assessed.

The comparison may be achieved in a variety of ways. For example, the comparison may be made by comparing a photograph of the coating after step (iii) with a photograph of the coating before step (iii). The photographs that are compared should be equivalent. In other words, the photograph should be taken with a camera positioned at the same relative position to the jaw assembly for the before and after photographs, utilising the same camera settings and the same lighting conditions.

The comparison between the photographs can be done digitally. A digital comparison can provide improved precision in the coverage comparison. Therefore, the coverage before the mastication step can be digitally quantified to determine an area or line of coverage and then the subsequent coverage after the mastication step can be digitally quantified to give a coverage area or line after the interaction with the chewable product. These two quantifications can then be compared to give a quantitative indication of the removal of the coating and thus an indication of the mechanical interaction of the chewable product with the teeth.

When making comparisons between the coating coverage before and after the interaction of the chewable product with the teeth it is useful for the coating to have a color that contrasts with the color underlying the coating. In this way, the presence or absence of the coating can be readily ascertained. In particular, it is advantageous for the coating to have a hue that can be isolated from the rest of the photograph when using digital image analysis techniques.

As noted above, the coating may be such that less than 4 newtons of normal force is required to remove it. Alternatively, less than 2 newtons of normal force may be required to remove the coating. Alternatively, less than 1.5 newtons of normal force may be required to remove the coating. Alternatively, less than 1 newton of normal force may be required to remove the coating. Further, less than 0.5 newtons of normal force may be required to remove the coating. In particular, 0.05 to 2 newtons of normal force may be required to remove the coating. In particular, 0.5 newtons to 2 newtons of normal force may be required to remove the coating. In particular, 1 newton to 2 newtons of normal force may be required to remove the coating. Such ranges of force ensure that the coating behaves in a similar manner to plaque.

Put another way, the coating may be such that less than 34.5 kPa (5 psi) of pressure is required to remove it. Alternatively, between 0.69 kPa and 34.5 kPa (between 0.1 and 5 psi) may be required to remove the coating. This ensures the coating behaves in a similar manner to plaque. In particular, the coating may require a removal pressure between 0.69 kPa and 6.9 kPa (0.1 and 1 psi). This represents the lower end of forces associated with tooth cleaning, or it may require pressure between 6.9 kPa and 34.5 kPa (between 1 and 5 psi). This represents the higher end forces associated with tooth cleaning.

The coating may be such that less than 689.5 kPa (100 psi) is required to remove it. Alternatively, between 172.4 kPa and 689.5 kPa (between 25 and 100 psi) may be required to remove it. This ensures the coating behaves in a similar manner to calculus. Overall, the coating may be such that a pressure of between 0.69 kPa and 689.5 kPa (between 0.1 and 100 psi), more preferably between 6.9 kPa and 689.5 kPa (between 1 psi and 100 psi) is required to remove it. This ensures the coating can behave in a similar manner to either plaque or calculus as required.

The use of paint as a plaque mimic is one possibility. It is also possible to form a plaque biofilm onto the surface of artificial teeth. Such teeth may be made from hydroxyapatite. In this way, the effect of the chewable product on plaque can be accurately assessed.

As noted above, step (iii) of the method of the present invention involves moving the jaws relative to each other in a mastication action so as to effect a chewing of the chewable product. The amount of chewing that is utilized can be varied as required.

For example, the mastication action may be chosen so as to reflect the amount of chewing that a given product will undergo in vivo. Therefore, the amount of time and the frequency of impact of the mastication action will reflect the amount of chewing that will be required in real life to break down or consume the product. This approach would give an indication of the expected lifetime of the chewable product. Alternatively, step (iii) may be carried out in the same manner for a range of chewable products so as to give a comparable indication of the interaction as a function of the number of chews and/or per unit time chewed.

There are various possible approaches for step (iii). A possible approach involves the jaw assembly being conceptually divided into a plurality of sections and the chewable product being placed in each section for a given amount of time. For example, the jaw assembly can be conceptually divided into three sections and the chewable product may be placed in each section for 20 seconds. The total time can be adjusted to reflect the in vivo lasting time. In a similar manner, the chewable product can be placed in each section for a given number of bites. Again, the total number of bites can be adjusted to reflect the in vivo lasting time.

The present invention further comprises an animal dentistry apparatus comprising a jaw assembly wherein the jaw assembly comprises a lower jaw and an upper jaw, wherein the jaw assembly is configured such that the lower jaw and the upper jaw can be moved apart and together in a mastication action, wherein the upper jaw comprises at least one tooth, and the lower jaw comprises at least one tooth; and a means to effect the mastication action wherein the means is configured to apply up to at least 50 kg of normal load to the jaw assembly, alternatively up to at least 100 kg, up to at least 250 kg, up to at least 500 kg, or up to at least 750 kg.

Such an animal dentistry apparatus can be used with the method described herein.

As noted above, the means, e.g., a hand or foot operated lever, pulley, or crank, or motor, to effect the mastication action is configured to apply up to at least 50 kg of normal load to the jaw assembly. The ability of the apparatus to work with these normal loads ensures that the apparatus is capable of replicating a range of animal bite forces and thus able to approximate the interaction between the chewable product and the teeth of an animal. The ability of the apparatus to work with normal loads of up to at least 500 kg ensures that the apparatus is capable of replicating a broad range of animal bite forces. Further, the ability of the apparatus to work with normal loads of up to at least 750 kg ensures that the apparatus is capable of fully replicating the full range of canine bite forces.

The means to effect the mastication action may be a hand or foot operated, or mechanical means. The means to effect the mastication action may comprise a motor connected to the jaw assembly so as to effect the relative motion between the upper and lower jaws.

One example of a motor that is particularly well suited to provide the mastication action to the jaw assembly is a universal testing machine. Such universal testing machines allow precise control over the applied forces and the rate of movement enabling a particular form of mastication to be enacted. Therefore, an automated jaw opening and closing procedure can be put into effect with applied normal loads of up to 500 kg, or 750 kg. A possible Universal Testing Machine is the Texture Analyser TA.HDplus-Stable Micro Systems, London.

The present invention further provides an animal dentistry apparatus comprising a jaw assembly, wherein the jaw assembly comprises a lower jaw and an upper jaw, wherein the jaw assembly is configured such that the lower jaw and the upper jaw can move apart and together in a mastication action, and wherein the upper jaw comprises at least one tooth, and the lower jaw comprises at least one tooth; the apparatus further comprises a coating on the at least one tooth in the upper jaw and/or at least one tooth in the lower jaw, wherein the coating is capable of being removed by a pressure of less than 689.5 kPa. Desirably, at least a portion of the animal dentistry apparatus will be manufactured and/or artificial.

In some embodiments, the animal dentistry apparatus may include a coating, provided in conjunction with at least a portion of the jaw assembly, the coating being useful to indicate the mechanical interaction of the jaw assembly with a chewable product.

As stated herein, the upper jaw comprises at least one tooth and the lower jaw comprises at least one tooth. In particular, the upper jaw may comprise a plurality of teeth where the at least one tooth referred to herein is one of the plurality of teeth in the upper jaw. Alternatively, the at least one tooth referred to herein may be a plurality of teeth. The plurality of teeth may be all of the teeth present in the upper jaw. Alternatively, the plurality of teeth may be a subset of the plurality of teeth that are present in the upper jaw. For example, when it is stated herein that the at least one tooth comprises a coating, that at least one tooth may be a plurality of teeth so that the plurality of teeth have a coating. Those plurality of teeth may be all of the teeth present in the upper jaw or just a subset of the plurality of teeth that are present in the upper jaw.

The lower jaw may comprise a plurality of teeth and the at least one tooth in the lower jaw is part of the plurality of teeth in the lower jaw. The features recited in relation to the plurality of teeth in the upper jaw above apply equally and independently to the at least one tooth and plurality of teeth in the lower jaw.

The upper jaw of the jaw assembly may have at least a portion that resembles at least a portion of the upper jaw of an animal. The upper jaw, or a portion thereof can be isolated from an animal, or be an ex vivo jaw bone or portion thereof. In other words, there can be a part of the upper jaw that is substantially similar to the appearance and the shape of part of the upper jaw of an animal. This can include the shape of a gum region. This can include at least some of any teeth that are present. Therefore, these teeth have a shape corresponding to those of the real animal. When a plurality of teeth are present the order of these teeth as well as their individual appearance will correspond to those in the animal. In this way, the upper jaw can replicate a portion of the animal's teeth and gums, which allows insight into how this portion of the animal's jaw interacts with a chewable product.

In a corresponding manner, at least a portion of the lower jaw can resemble at least a portion of the lower jaw of an animal. The lower jaw, or a portion thereof can be isolated from an animal, or be an ex vivo jaw bone or portion thereof. In this regard, the features described in relation to the upper jaw equally and independently apply to the lower jaw.

At least a portion of the upper jaw may resemble the upper jaw of the animal of interest. This may include a complete set of teeth that resemble the teeth of the animal. The same can equally and independently apply to the lower jaw.

When the lower and/or upper jaw contains a portion that completely resembles the lower and/or upper jaw of the animal, the apparatus provides the ability to assess the interaction of a chewable product with all teeth that are present in the jaws of the animal of interest.

The upper jaw and the lower jaw of the jaw apparatus may be pivotally connected to each other at a pivot point. By being pivotally connected to each other the upper jaw and the lower jaw can move in a mastication action similar to an animal. Where the at least one tooth in the upper jaw and/or lower jaw resembles an animal tooth, the pivot point may be positioned at the anatomically correct position so that the bite action of the at least one tooth corresponds to the bite action for the animal. This has the advantage of replicating the actual mastication effect and so provides an insight into the actual experience on the chewable product when chewed by the corresponding animal.

The jaw assembly may be configured so that the upper jaw or lower jaw pivots relative to the lower jaw or upper jaw respectively in response to a linear motion applied to the jaw assembly. Being configured in this way, allows the jaw assembly to be easily manipulated to effect a mastication action, since it does not require any complex motions. Further, it allows the jaw assembly to operate when connected to a linear universal testing machine. The linear motion applied to the jaw assembly may be approximately 10 mm/s. Alternatively, the linear motion can be in the range of 0.01 to 40 mm/s, or 5 mm/s to 20 mm/s.

In order to pivot in response to a linear motion, one of the lower or upper jaws can comprise a bar pivotally attached to the section of the lower or upper jaw that has the at least one tooth. This bar is in turn pivotally attached to a handle. In this way, linear movement of the handle causes the pivotal motion of the mastication action. The bar may be pivotally attached above or below the section of the lower or upper jaw that has the at least one tooth. Alternatively, the bar may be pivotally attached at the other side of the pivot point between the upper and lower jaw, relative to the section comprising the at least one tooth.

One of the upper jaw or lower jaw may be fixed in position while the other jaw pivots relative to that jaw. In particular, the upper jaw may be fixed in position while the lower jaw pivots relative to this upper jaw during the mastication action. The arrangement having a fixed upper jaw and a moveable lower jaw corresponds to the situation seen in many animals, for example canines. Therefore, this allows the jaw assembly to replicate the bite action seen in vivo.

In relation to the jaw assembly, the lower jaw and/or the upper jaw may comprise separate components. In particular, the lower jaw and/or the upper jaw can comprise a jaw base and a jaw toothed section wherein the toothed section comprises the at least one tooth or the plurality of teeth when present. The toothed section may be removable from the jaw base. Further, the toothed section may comprise a portion that resembles a portion of the jaw of the animal when this feature is present. The ability to remove the jaw toothed section from the jaw base means that a variety of tooth arrangements can be utilized with a given jaw assembly. Accordingly, the jaw assembly can have universal jaw bases while having specific jaw toothed sections that replicate a variety of different animals. For example, even within one form of animal such as canine, there can be a variety of toothed sections which corresponds to different breeds and/or different sizes of canine. This increases the flexibility of the jaw apparatus of the present invention.

The toothed sections of the jaw assembly may be removably attached to the base sections via screw fixings.

Figure 1:
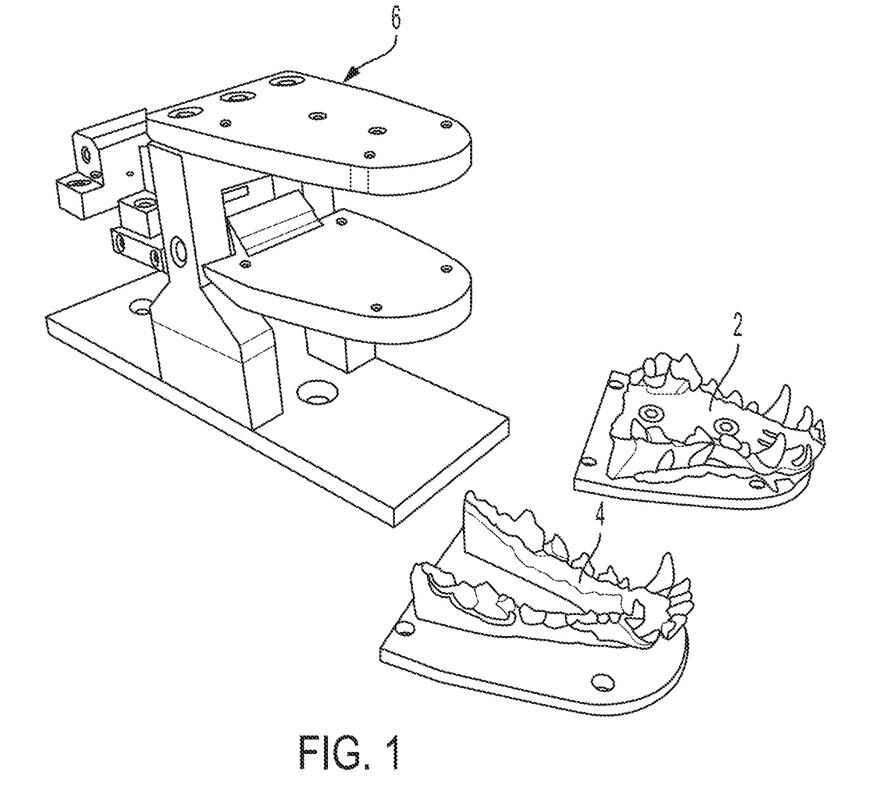
FIG. 1 is a photograph of a jaw assembly according to one embodiment, where the toothed sections of the upper jaw and the lower jaw are removed.

One method of manufacturing the jaw assembly and or dentistry apparatus described herein involves electrically scanning a canine's skull to create a 3D image. This image is then digitally modified to isolate the teeth including the surrounding jaw. The image is then 3D sintered/printed to form a metallic replica of the canine jaw with a scale of 1:1. This results in an upper jaw toothed section (2) and a lower jaw toothed section (4) for use as a jaw assembly (6). The upper jaw toothed section (2) and the lower jaw toothed section (4) are shown separate from the rest of the jaw assembly in FIG. 1.

Figure 2:
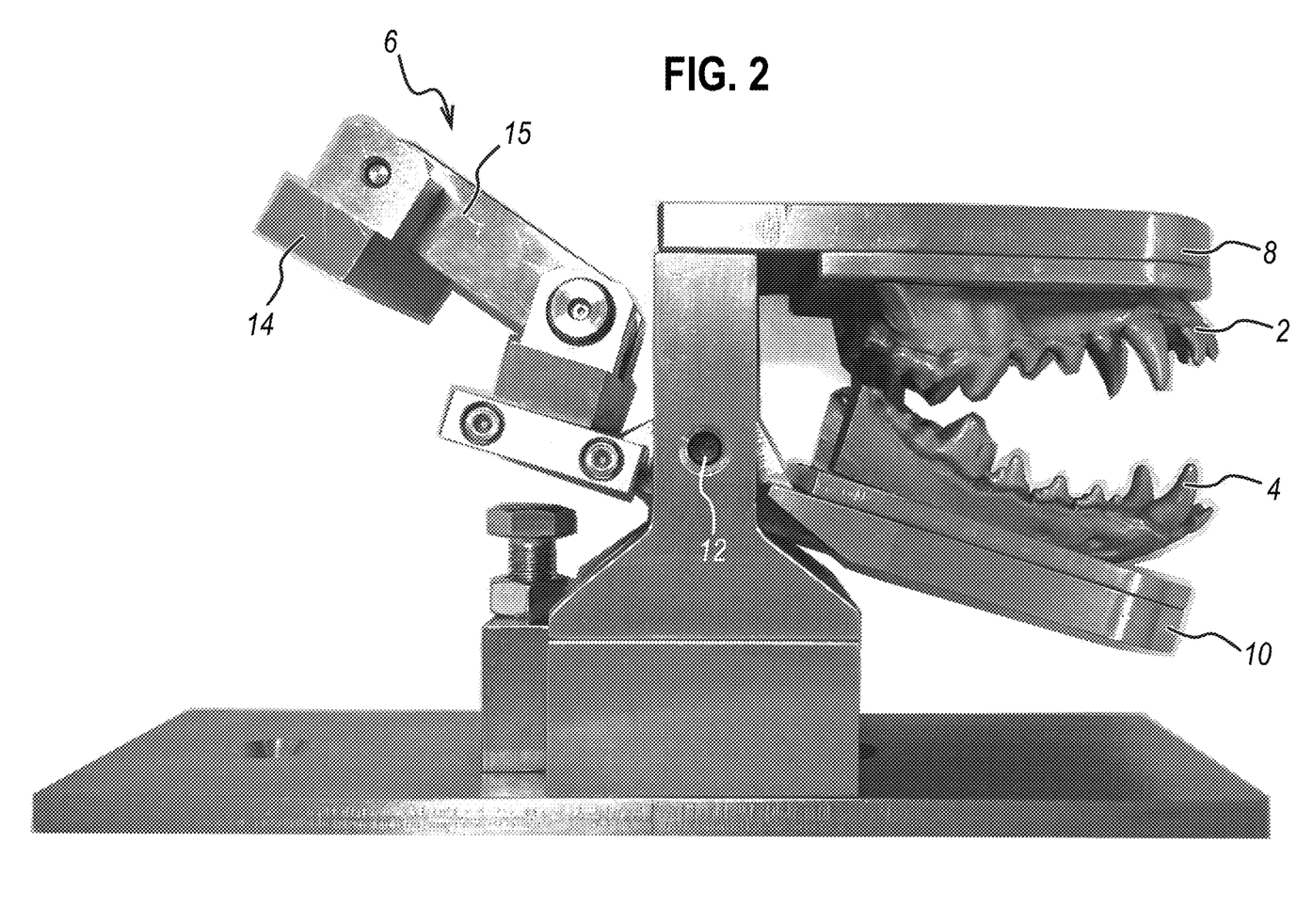
FIG. 2 is a photograph of the jaw assembly of FIG. 1, with the toothed sections of the upper jaw and the lower jaw attached.

FIG. 2 depicts the jaw assembly (6) which incorporates the upper jaw toothed section (2) and the lower jaw toothed section (4). The jaw assembly further comprises the upper jaw base (8) and the lower jaw base (10). Accordingly, the upper jaw comprises both the upper jaw toothed section (2) and the upper jaw base section (8), while the lower jaw comprises the lower jaw toothed section (4) and the lower jaw base (10).

The upper jaw base (8) is pivotally connected to lower jaw base (10) at pivot point (12). The pivot point (12) is positioned so that it is in the anatomically correct position for the upper jaw toothed section (2) and the lower jaw toothed section (4).

The upper jaw toothed section (2) and the lower jaw toothed section (4) are removably attached to the respective jaw bases by screws. Accordingly, the upper jaw toothed section (2) and the lower jaw toothed section (4) may be replaced and substituted as required with other upper jaw toothed sections and lower jaw toothed sections.

The jaw assembly (6) can be moved in a mastication action by applying a linear motion to handle (14). The handle (14) is pivotally attached to a bar (15) which in turn is pivotally attached to lower jaw base (10).

Figure 3:
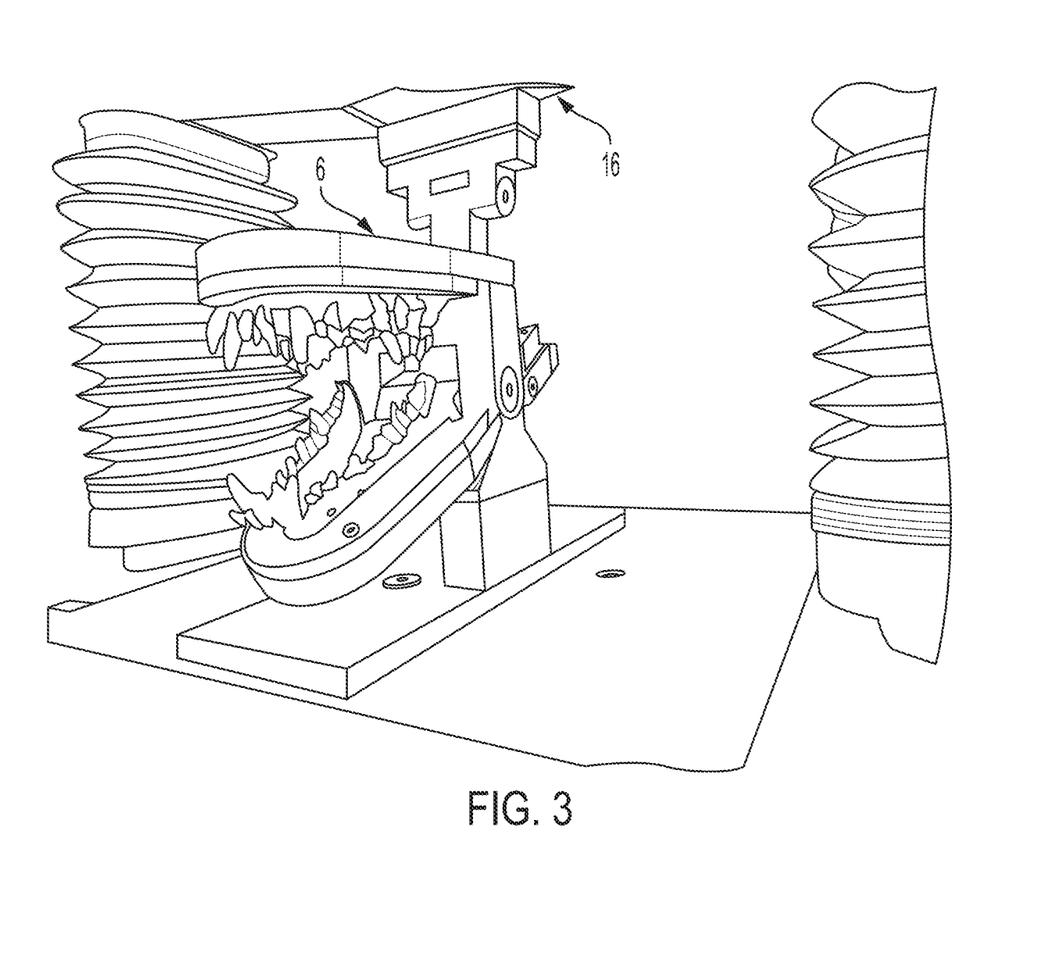
FIG. 3 is a photograph of the jaw assembly shown in FIG. 2 attached to a linear universal testing machine.

FIG. 3 depicts the jaw assembly (6) connected to a universal testing machine (16) (Texture Analyser TA.HDplus-Stable Micro Systems, London).

Figure 4A:
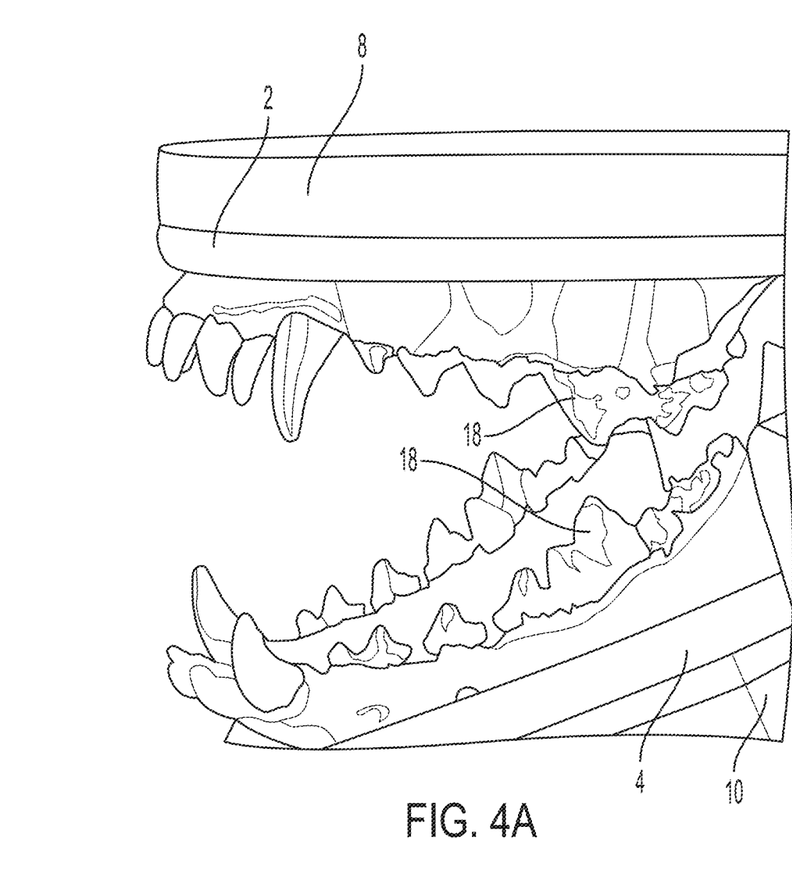
FIG. 4A is a photograph of the jaw assembly of FIG. 2 with a coating applied to all or a portion of one or more of the teeth prior to interaction with the chewable product.
Figure 4B:
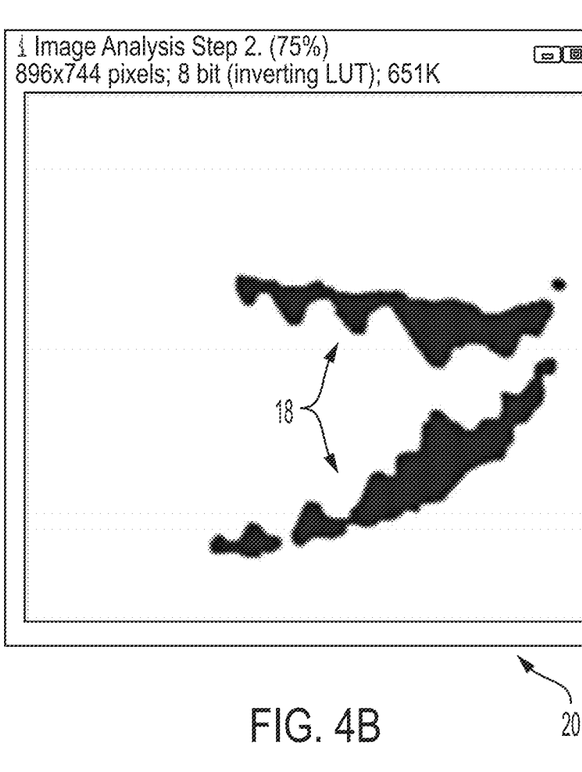
FIG. 4B is the digital image analysis showing the digital isolation of the coating for quantifying the coverage area.

As depicted in FIG. 4A, a coating (18) is applied to a subset of the teeth in both the upper jaw and lower jaw. FIG. 4B depicts digial image analysis (2) showing the digital isolation of the coating (18) for quantifying the coverage area.

EXAMPLES

Example 1 (Reference)

A key part of the development of periodontal disease is the accumulation of plaque specifically at the gingival margin. The Gingival Contour Plaque Index (GCPI) test is a rapid in vivo assessment of efficacy that is performed using conscious animals throughout. The length of plaque at the gum line is visualized with disclosing solution and measured using bespoke rules with 2 mm gradations curved to that typical for several groups of tooth type, such as incisors, canines and premolars. Starting with a clean mouth (teeth brushed and plaque baseline level checked), the build-up of gingival plaque is measured following a defined period of time exposed to a control diet with or without a test oral care product. In each case, the total number of calories are controlled and fixed, the assessors are blinded as to which dog(s) has/have received the test oral care product, and the dogs are split into groups typically using cross-over statistical designs.

A GCPI trial was conducted comparing 3 chew samples of equivalent mass and calories. The three chews were produced from the same recipe but underwent different processing to alter their density:

a. 4005—High density b. 4006—Medium density c. 4007—Low density

The products were fed to panel of 12 medium-sized Beagles according to the design given in Table 1.

TABLE 1

| Dog | Phase 1 | Phase 2 | Phase 3 |
| --- | --- | --- | --- |
| Silvester | 4005 | 4007 | 4006 |
| Elliot | 4005 | No Chew | 4006 |
| Aura | 4005 | No Chew | 4007 |
| Gretchen | 4006 | No Chew | 4005 |
| Franzl | 4006 | 4005 | 4007 |
| Xaverl | 4006 | 4007 | No Chew |
| Dobby | 4007 | 4006 | 4005 |
| Myrte | 4007 | 4005 | No Chew |
| Wally | 4007 | 4006 | No Chew |
| Neville | No Chew | 4007 | 4005 |
| Manni | No Chew | 4005 | 4006 |
| Bagle | No Chew | 4006 | 4007 |

GCPI values were recorded then processed according to the following:

GCPI value=gingival contour plaque index (length of plaque measured on the tooth adjacent to the gumline)

$$ITS = \text{Individual tooth score} = \frac{GCPI \text{ value}}{\text{length of gingival margin}}$$

$$WMS = \text{whole mouth score} = \frac{\sum ITS}{\text{Number of teeth scored}}$$

$$PI = \text{plaque index} = WMS_{after\ phase} - WMS_{before\ phase}$$

$$\text{Chew efficacy} = 100 \cdot \frac{PI_{no\ chew} - PI_{chew}}{PI_{no\ chew}}$$

Chew efficacy values calculated using the equations above are given in Table 2:

TABLE 1

| | Product Name | | | |
|---|---|---|---|---|
| | 4005 | 4006 | 4007 | No Chew |
| Dog | | | | |
| Bagle | 45.18 | 53.81 | 43.89 | 68.35 |
| Gretchen | 30.56 | 40.05 | 33.59 | 48.69 |
| Aura | 51.30 | 47.43 | 45.25 | 80.38 |
| Myrte | 48.23 | 38.59 | 39.69 | 60.77 |
| Neville | 28.93 | 42.17 | 31.01 | 57.77 |
| Silvester | 45.41 | 50.02 | 44.09 | 66.00 |
| Dobby | 49.43 | 39.03 | 43.72 | 48.31 |
| Elliot | 30.81 | 60.18 | 45.55 | 66.89 |
| Wally | 40.91 | 29.38 | 30.57 | 59.25 |
| Xaverl | 60.78 | 27.67 | 45.31 | 71.14 |
| Manni | 43.12 | 38.92 | 31.59 | 48.63 |
| Franzl | 53.33 | 26.51 | 34.77 | 55.23 |
| Mean Plaque Index | | | | |
| Scores | 44.00 | 41.15 | 39.09 | 60.95 |
| Chew Efficacy | 28% | 32% | 36% | |

Example 2

The in vitro oral care model uses a 3D sintered/printed jaw assembly of the present invention made from 316L stainless steel that is a 1:1 representation of a medium-sized mesaticephalic dog including position of its jaw articulation (hinge point). The jaw assembly is attached to a Texture Analyser TA.HDplus-Stable Micro Systems, London. The motions of the lower jaw are defined to mimic a chewing process. The Texture Analyser is set to the standard test speed of 10 mm/s resulting in approximately 18 bites/min. A blue open acrylic paint (Golden Open Acrylic Cobalt Blue, Golden Artist Colors, Inc., New Berlin, N.Y. 13411-6154) is applied with a paint brush to the surface of the teeth to be analysed. It was found that this paint required only 100 g of force to be removed even after 20 minutes of drying time (the time frame of the experiments).

Figure 6:
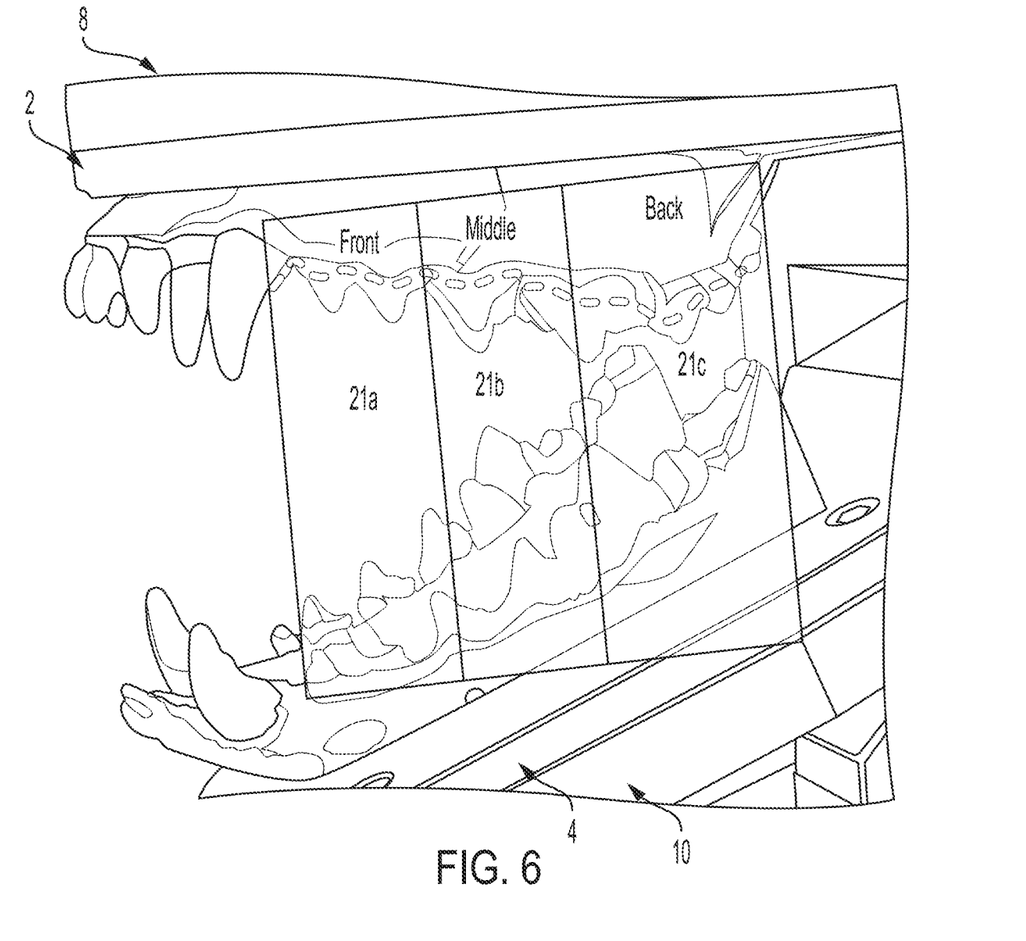
FIG. 6 depicts the possible division of teeth of the jaw assembly of FIG. 2 in relation to a testing procedure.

Products were positioned and held by hand in the jaw assembly using the 4 different protocols outlined below which makes use of FIG. 6 where the jaw is divided into 3 regions; front (21a), middle (21b), and back (21c). In each case, only premolars and molars were assessed, and only on one side of the jaw.

Approach 1 (A)

Feed one side of the jaw for 1 minute, spending approximately 20 seconds in each third of the mouth repositioning the product whilst ensuring consistency across replications and different products.

Approach 2 (B)

The same as approach 1 but for the duration of the product's lasting time according to in vivo data. In this case, lasting time was measured as 54 seconds for 4005, and 98 seconds for 4007. Product 4006 was not assessed for lasting time and so was not subjected to this in vitro method.

Approach 3 (D)

Three bites of the product are carried out in each third of the mouth and so a total of 9 bites per test. The test was paused after the three bites in each third of the mouth so as to allow repositioning of the product before restarting.

Approach 4 (F)

As for Approach 3 above but scale-up to match lasting time for each product: 11 bites for 4005 and 29 bites for 4007.

Two principally different methods were used to measure plaque level and provide an efficacy score, both of which made use of photographs of the model before and after the products were exposed to the jaw assembly.

Measure Plaque Mimic Area

Figure 5A:
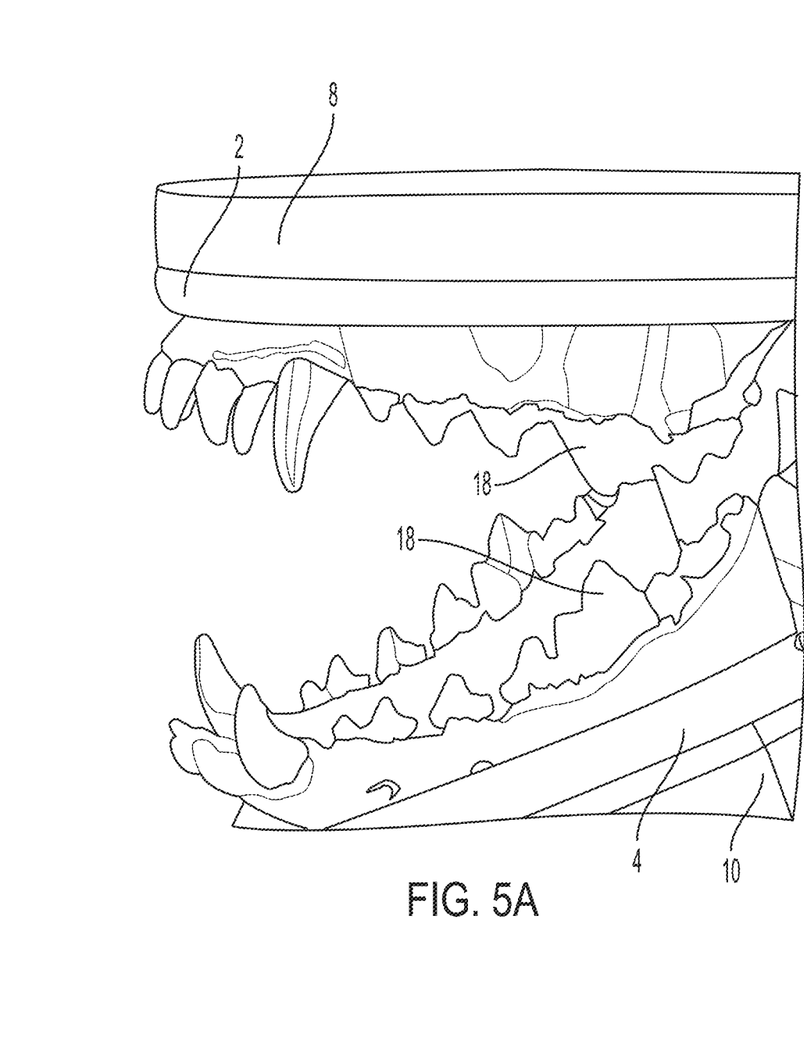
FIG. 5A is a photograph of the jaw assembly shown in FIG. 4A, after interaction of the chewable product with the jaw assembly.
Figure 5B:
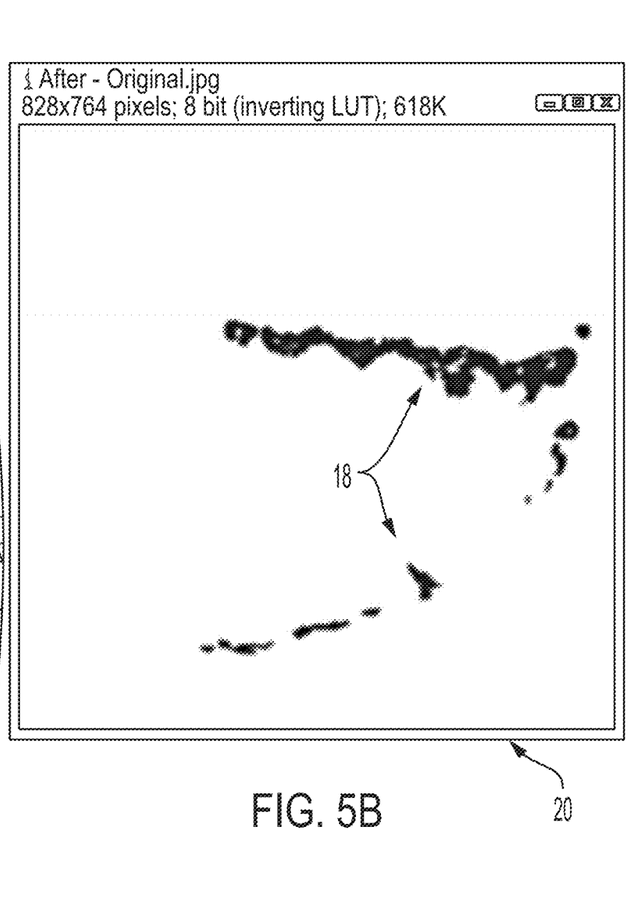
FIG. 5B is the digital image analysis showing digital isolation of the coating for quantifying the coverage area.

For this method, the area of plaque mimic (the blue acrylic paint) is quantified both before and after feeding a test product to the in vitro model. FIG. 4A depicts the plaque mimic coating (18) before the testing procedure. FIG. 4B depicts digital image analysis (20) showing the digital isolation of the plaque mimic coating (18) before the testing procedure. FIG. 5A depicts the plaque mimic coating (18) of FIG. 4A after the testing procedure. FIG. 5B depicts digital image analysis (20) showing the digital isolation of the plaque mimic coating (18) of FIG. 5A after the test procedure.

The percentage of plaque mimic reduction is then measured and used to represent product in vitro efficacy.

$$i.\ InVitro\ \text{oral care efficacy (plaque area removed)} = 100 \cdot \frac{P_{Before} - P_{After}}{P_{Before}}$$

1. where P=number of pixels representing plaque mimic

Measure Plaque-Mimic Length at the Gingival Margin

Figure 7:
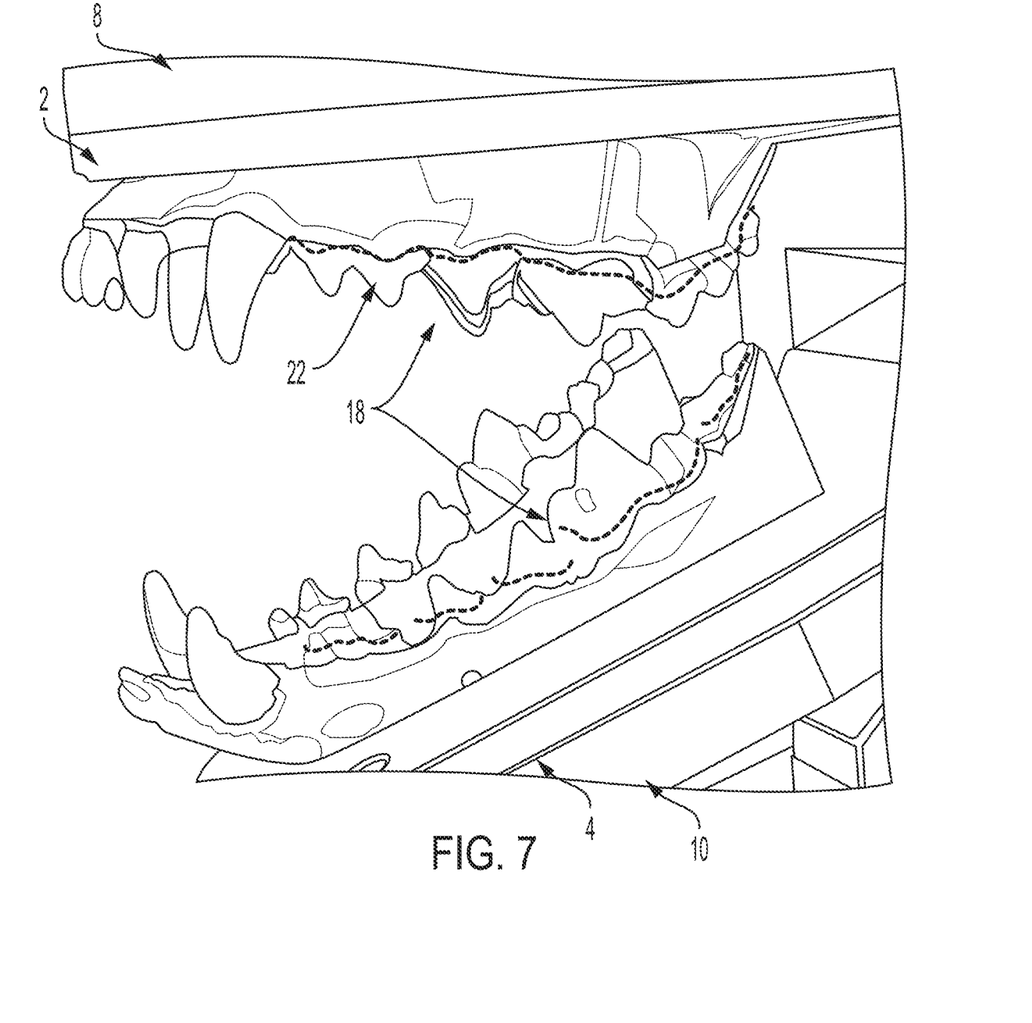
FIG. 7 depicts the lines for measuring the presence of plaque along the gum line of the jaw assembly of FIG. 2.

For this method, FIG. 7 was created to provide gradations across the expected gum-line (22) (since the model was based on a canine skull its gum-line was not present and so its position was estimated). Similarly to the in vivo GCPI method, the length of plaque mimic coating (18) present across the gum line for each tooth was measured and expressed as a ratio of the total tooth gum line length.

$$ITS = \text{Individual tooth score} = \frac{\text{Gingival plaque mimic length}}{\text{length of gingival margin}}$$

$$WMS = \text{whole mouth score} = \frac{\sum ITS}{\text{Number of teeth scored}}$$

$$PI = \text{plaque index} = WMS_{after\ phase}$$

$$InVitro\ GCPI\ \text{efficacy (gingival plaque length removed)} = 100 \cdot (1 - PI)$$

Results

Table 3 shows all data, both in vivo and in vitro, for the products 4005/6/7 as described above.

The in vivo test does not assess all of the dog's teeth largely due to accessibility on conscious dogs. The in vitro method also did not measure all teeth, specifically the incisors and canines were not assessed. For this reason, data is also shown for comparable teeth only, i.e. only those teeth common to both in vivo and in vitro protocols.

TABLE 2

| | | Efficacy Values (%) | | | |
|---|---|---|---|---|---|
| | | | | Product Name | |
| | | Procedure Used | 4005 | 4006 | 4007 |
| All measured teeth* | In-vivo (GCPI) efficacy | | 28% | 32% | 36% |
| | In-vitro plaque area removal efficacy | A | 55% | 64% | 59% |
| | | B | 57% | — | 64% |
| | | D | 40% | 37% | 42% |
| | | F | 42% | — | 48% |

TABLE 2-continued

Efficacy Values (%)

| | | Procedure Used | 4005 | 4006 | 4007 |
|---|---|---|---|---|---|
| | In-vitro gum-line removal efficacy | A | 42% | 42% | 48% |
| | | B | 48% | — | 56% |
| | | D | 15% | 16% | 19% |
| | | F | 27% | — | 28% |
| Only Comparable teeth ie Lower premolar 2/3/4; Upper premolar 1/2/3/4 | In-vivo (GCPI) efficacy | | 32% | 41% | 48% |
| | In-vitro gum-line removal efficiacy | A | 39% | 39% | 40% |
| | | B | 47% | — | 61% |
| | | D | 16% | 18% | 20% |
| | | F | 29% | — | 37% |

Comparison with In Vivo Approach

The strongest correlation between in vivo and in vitro data was observed with the following conditions:

Representing in vitro data in terms of gumline plaque-mimic removal (rather than whole tooth plaque-mimic area removal)

Only considering comparable teeth (i.e. those assessed in both the in vitro and in vivo methods)

Fixing the number of bites that the model applies at each region of the mouth

The fact that the strongest correlation was observed with those criteria is believed to be due to both approaches assessing gingival plaque length, the same teeth and using a consistent and objective in vitro testing procedure.

The in vitro test methods that used actual lasting time data were not considered as part of the correlation between in vitro and in vivo because there were only 2 data points.

Figure 8:
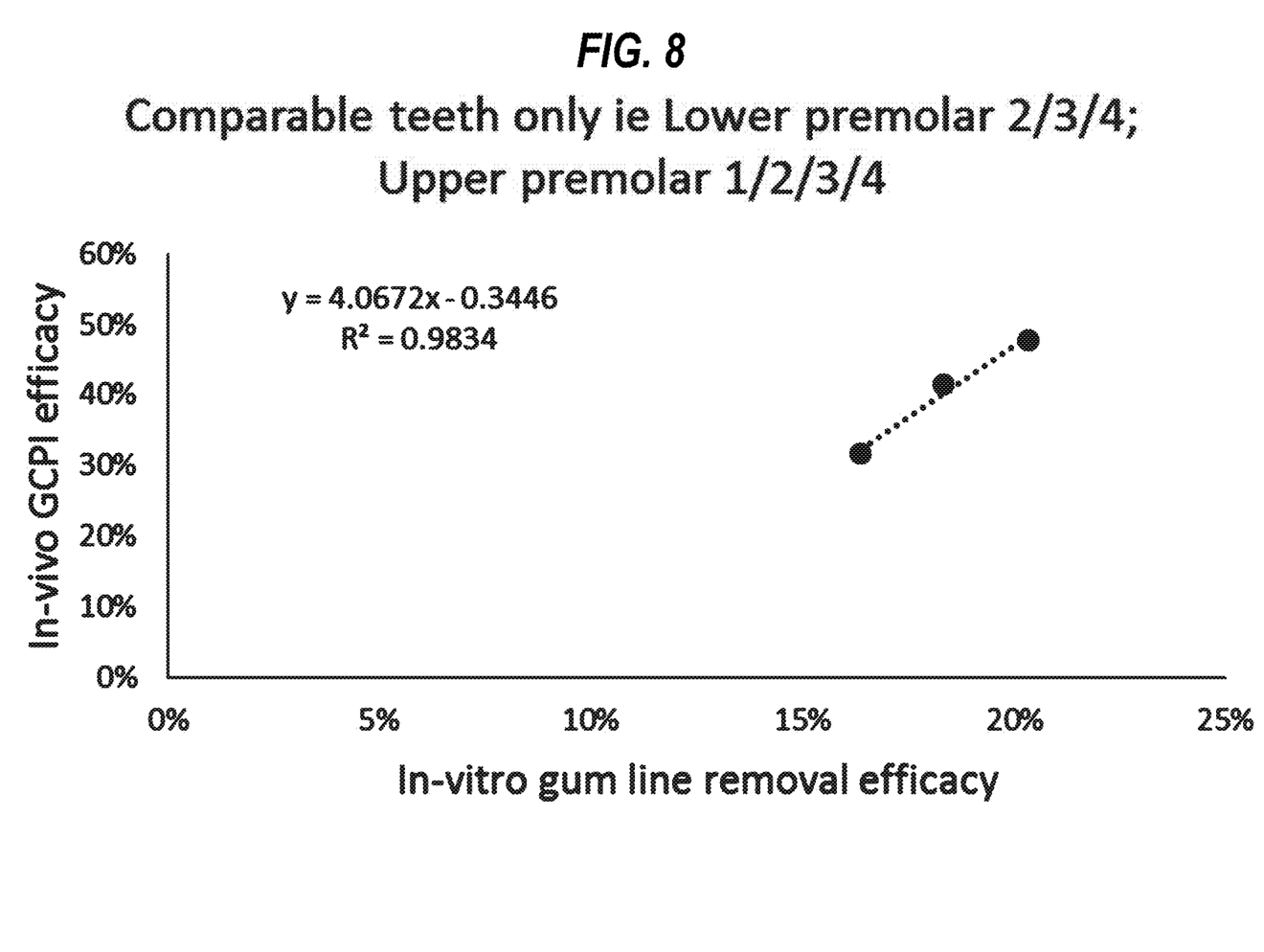
FIG. 8 depicts the correlation between in vivo and in vitro methods of testing.

FIG. 8 depicts the correlation between in vitro (gumline plaque mimic removal) and in vivo (GCPI) when only considering teeth that were assessed in both the in vivo and in vitro tests.

A discrepancy can be observed in the absolute efficacy values reported in the in vivo and in vitro data; specifically, the in vitro data tended to yield lower values. This is believed to be due to the in vitro test measuring plaque-mimic reduction, whereas the in vivo test starts with a clean mouth and measures the prevention of plaque build-up over, in this case, a 3 day period. Nevertheless, the presence of a correlation validates the use of the in vitro model as an approach for gauging relative effectiveness of a range of chewable products without the need to go to the expense and time of conducting full in vivo tests for every possible product of interest.

The forgoing describes specific embodiments of the present invention. However, these should not be considered limiting. The invention is defined by the following claims.

The invention claimed is:

1. An animal dentistry apparatus comprising:
   a jaw assembly, wherein the jaw assembly comprises a lower jaw and an upper jaw, wherein the jaw assembly is configured such that the lower jaw and the upper jaw can move apart and together in a mastication action, and wherein the upper jaw comprises at least one tooth, and the lower jaw comprises at least one tooth, and wherein the at least one tooth comprises a coating configured to be removed by application of pressures between 0.69 kPa and 689.5 kPa; and
   a hand or foot operated mechanism, or motor, that effects the mastication action, wherein the mechanism or motor is configured to apply up to at least 50 kg of normal load to the jaw assembly.

2. The animal dentistry apparatus of claim 1, wherein the motor is configured to apply up to at least 750 kg of normal load to the jaw assembly.

3. The animal dentistry apparatus of claim 1, wherein the motor comprises a universal testing apparatus.

4. The animal dentistry apparatus of claim 1, wherein the coating comprises acrylic paint.

5. A method for assessing a chewable product, comprising the steps of:
   (i) providing a jaw assembly, wherein the jaw assembly comprises a lower jaw and an upper jaw, wherein the jaw assembly is configured such that the lower jaw and the upper jaw can move apart and together in a mastication action, and wherein the upper jaw comprises at least one tooth, and the lower jaw comprises at least one tooth;
   (ii) placing the chewable product between the upper jaw and the lower jaw of the jaw assembly;
   (iii) using a hand or foot operated mechanism, or motor, to move the jaws relative to each other in the mastication action in order to impact the at least one tooth of the upper jaw and the at least one tooth of the lower jaw onto the chewable product; and
   (iv) assessing a coating by comparing coverage of a coating after step (iii) with coverage of a coating before step (iii).

6. The animal dentistry apparatus of claim 1, wherein at least one tooth, or at least one of the upper or lower jaw is isolated from an animal.

7. The animal dentistry apparatus of claim 1, wherein the upper jaw comprises a plurality of teeth and the at least one tooth in the upper jaw is at least part of the plurality of teeth in the upper jaw, and the lower jaw comprises a plurality of teeth and the at least one tooth in the lower jaw is at least part of the plurality of teeth in the lower jaw.

8. The animal dentistry apparatus of claim 7, wherein
   at least a portion of the upper jaw is artificial and resembles at least a portion of the upper jaw of an animal, and the at least a portion of the upper jaw comprises the plurality of teeth; and/or
   at least a portion of the lower jaw resembles at least a portion of the lower jaw of the animal, and the at least a portion of the lower jaw comprises the plurality of teeth.

9. The animal dentistry apparatus of claim 8, wherein the animal is selected from one of a canine or a feline.

10. The animal dentistry apparatus of claim 8, wherein the upper jaw and the lower jaw are pivotally connected to each other at a pivot point.

11. The animal dentistry apparatus of claim 10, wherein the jaw assembly is configured so that the upper jaw or lower jaw pivots relative to the lower jaw or upper jaw respectively in response to a linear motion applied to the jaw assembly.

12. The animal dentistry apparatus of claim 11, wherein the upper jaw is fixed in position, while the lower jaw pivots relative to the upper jaw in response to a linear motion applied to the jaw assembly.

13. The animal dentistry apparatus of claim 7, wherein at least one of the plurality of teeth is removable from the upper jaw and/or lower jaw.

14. The method of claim 5, wherein comparing coverage of a coating comprises digitally comparing a photograph of the coating after step iii with a photograph of the coating before step iii.

15. The method of claim 5, further comprising the step, prior to step (ii), of providing a coating on the at least one tooth in the upper jaw and/or the at least one tooth in the lower jaw.

16. An animal dentistry apparatus comprising:
a jaw assembly wherein the jaw assembly comprises a lower jaw and an upper jaw, wherein the jaw assembly is configured such that the lower jaw and the upper jaw can move apart and together in a mastication action, wherein the upper jaw comprises at least one tooth, and the lower jaw comprises at least one tooth, wherein the at least one tooth comprises a coating configured to be removed by application of pressures between 0.69 kPa and 689.5 kPa, and wherein at least a portion of the jaw assembly is artificial or manufactured; and
- a means to effect the mastication action, wherein the means is configured to apply up to at least 50 kg of normal load to the jaw assembly.

* * * * *